(12) United States Patent
Link et al.

(10) Patent No.: US 9,333,089 B2
(45) Date of Patent: May 10, 2016

(54) INTERVERTEBRAL FUSION IMPLANT (71) Applicant: WALDEMAR LINK GmbH & Co. KG, Hamburg (DE)

(72) Inventors: Helmut D. Link, Hamburg (DE); Klaus Dmuschewsky, Hamburg (DE)

(73) Assignee: WALDEMAR LINK GmbH & Co., KG, Hamburg (DE)

( * ) Notice: Subject to any disclaimer, the term of this patent is extended or adjusted under 35 U.S.C. 154(b) by 433 days.

(21) Appl. No.: 13/918,464

(22) Filed: Jun. 14, 2013

(65) Prior Publication Data

US 2014/0005787 A1    Jan. 2, 2014

Related U.S. Application Data (60) Provisional application No. 61/659,622, filed on Jun. 14, 2012.

(51) Int. Cl.
*A61F 2/44* (2006.01)
*A61F 2/46* (2006.01)
*A61F 2/30* (2006.01)

(52) U.S. Cl.
CPC .............. *A61F 2/4455* (2013.01); *A61F 2/442* (2013.01); *A61F 2/4465* (2013.01); *A61F 2/4611* (2013.01); *A61F 2/30965* (2013.01); *A61F 2002/30014* (2013.01); *A61F 2002/30016* (2013.01); *A61F 2002/3093* (2013.01); *A61F 2002/30163* (2013.01); *A61F 2002/30365* (2013.01); *A61F 2002/30367* (2013.01); *A61F 2002/30373* (2013.01); *A61F 2002/30383* (2013.01); *A61F 2002/30492* (2013.01);

(Continued)

(58) Field of Classification Search
CPC . A61F 2/4455; A61F 2002/443; A61F 2/442; A61F 2/30965; A61F 2/4465; A61F 2/4611
USPC ............................................. 623/17.11–17.16
See application file for complete search history.

(56) References Cited

U.S. PATENT DOCUMENTS

| | | | |
|---|---|---|---|
| 2002/0128716 A1* | 9/2002 | Cohen ....................... | A61F 2/44 623/17.15 |
| 2003/0139813 A1 | 7/2003 | Messerli et al. | |

(Continued)

FOREIGN PATENT DOCUMENTS

| | | |
|---|---|---|
| EP | 1 293 180 | 3/2003 |
| WO | WO-00/30568 | 6/2000 |

(Continued)

*Primary Examiner* — Christopher Beccia
*Assistant Examiner* — Diana S Jones
(74) *Attorney, Agent, or Firm* — Morrison & Foerster LLP (57) ABSTRACT

An intervertebral fusion implant for the fusion of two vertebrae comprises an upper bearing body for placing on a lower end-plate of a vertebra, a lower bearing body for placing on an upper end-plate of a vertebra, and a central piece arranged between the bearing bodies. The central piece comprises a claw coupling which, in a coupling position, couples the two bearing bodies in a rotationally fixed manner to each other. In an open position of the claw coupling, the bearing bodies are freely movable in relation to each other. The claw coupling is actuated automatically via a plastic blocking body which, in its initial position, holds the claw coupling open and, under a load transferred from one vertebra to the other vertebra, is slowly deformable until it reaches a final coupling position in which the claw coupling is closed. This results in the slow fusion of the vertebrae.

28 Claims, 5 Drawing Sheets

(52) U.S. Cl.
CPC ............ *A61F2002/30523* (2013.01); *A61F 2002/30538* (2013.01); *A61F 2002/30556* (2013.01); *A61F 2002/30599* (2013.01); *A61F 2002/30607* (2013.01); *A61F 2002/30616* (2013.01); *A61F 2002/30682* (2013.01); *A61F 2002/30822* (2013.01); *A61F 2002/30845* (2013.01); *A61F 2002/30846* (2013.01); *A61F 2002/30884* (2013.01); *A61F 2002/30896* (2013.01); *A61F 2002/30973* (2013.01); *A61F 2002/4628* (2013.01); *A61F 2310/00023* (2013.01); *A61F 2310/00029* (2013.01); *A61F 2310/00035* (2013.01); *A61F 2310/00179* (2013.01)

(56) References Cited

U.S. PATENT DOCUMENTS

| 2003/0216810 A1* | 11/2003 | Ralph | A61F 2/4425 623/17.14 |
| 2004/0024461 A1* | 2/2004 | Ferree | A61F 2/34 623/17.13 |
| 2004/0127991 A1* | 7/2004 | Ferree | A61F 2/4425 623/17.11 |
| 2005/0015152 A1* | 1/2005 | Sweeney | A61F 2/4425 623/17.14 |
| 2005/0197703 A1* | 9/2005 | Diaz | A61F 2/4425 623/17.13 |
| 2006/0015183 A1* | 1/2006 | Gilbert | A61F 2/4425 623/17.11 |
| 2006/0089714 A1* | 4/2006 | Liu | A61F 2/4425 623/17.11 |
| 2006/0116769 A1* | 6/2006 | Marnay | A61F 2/4425 623/17.15 |
| 2006/0136062 A1* | 6/2006 | DiNello | A61F 2/4425 623/17.14 |
| 2006/0142862 A1* | 6/2006 | Diaz | A61F 2/4611 623/17.13 |

FOREIGN PATENT DOCUMENTS

| WO | WO-02/09626 | 2/2002 |
| WO | WO-2006/043138 | 4/2006 |

* cited by examiner

INTERVERTEBRAL FUSION IMPLANT

REFERENCE TO RELATED APPLICATIONS

This application claims the benefit of U.S. Provisional Patent Application No. 61/659,622, filed on Jun. 14, 2012, the contents of which are incorporated herein by reference.

FIELD OF THE INVENTION

The invention relates to an intervertebral fusion implant for the fusion of two vertebrae, comprising an upper bearing body for placing on a lower end-plate of a vertebra, and a lower bearing body for placing on an upper end-plate of an opposite vertebra, and also a central piece arranged between the bearing bodies. The invention further relates to a system composed of an intervertebral fusion implant and of forceps, and to a method for insertion of the intervertebral fusion implant.

BACKGROUND OF THE INVENTION

An intervertebral disk may suffer degeneration as a result of injury, wear and disease, in which case it often exerts pressure on the nerve fibers of the spinal cord. This can cause severe pain or numbness in the extremities, and even symptoms of paralysis. It may therefore become necessary to remove the degenerated intervertebral disk. However, contact between the vertebrae still has to be avoided, since pain is otherwise caused by the friction between the end-plates of the vertebrae. There may also be medical grounds for avoiding in future a relative movement of the vertebrae that adjoin the degenerated intervertebral disk. In these cases, the degenerated intervertebral disk is replaced by an intervertebral fusion implant, which prevents a relative movement of the vertebrae.

Known intervertebral fusion implants have bearing bodies for placing on the end-plates of an upper and a lower vertebra. They are either inserted directly between the end-plates of two vertebrae or into grooves that have been drilled into the end-plates, with bone substance of the vertebrae being removed. The known implants fuse the two vertebrae bearing on them directly after the implantation. A disadvantage of these implants is that the patient suddenly has to adjust to the limited mobility of his spinal column. On the one hand, he notices the limitation through the implant. On the other hand, his locomotor apparatus also has to adapt immediately to the new situation. Thus, even directly after the operation, the ligaments and muscles of the spinal column are still designed to move the two fused vertebrae. In the period after the operation, this can prolong the phase of acclimatization and rehabilitation of the patient. Moreover, in the phase of acclimatization, the implant is exposed to greater mechanical loads than afterward.

SUMMARY OF THE INVENTION

An object of the invention is therefore to avoid the above-mentioned disadvantages.

A solution according to the invention lies in the features as broadly described herein. Advantageous developments are the subject matter of the detailed embodiments described below.

According to the invention, an intervertebral fusion implant for the fusion of two vertebrae is provided, comprising an upper bearing body for placing on a lower end-plate of a vertebra, and a lower bearing body for placing on an upper end-plate of an opposite vertebra, and also a central piece arranged between the bearing bodies, wherein the central piece is designed as a claw coupling which, in a coupling position, couples the two bearing bodies in a rotationally fixed manner to each other, wherein, in an open position of the claw coupling, the bearing bodies are freely movable in relation to each other, wherein the claw coupling is actuated automatically and has, as actuating member, a plastic blocking body which, in its initial position, holds the claw coupling open and, under a load transferred from one vertebra to the other vertebra, is slowly deformable until it reaches a final coupling position, in which the claw coupling is closed.

A few terms will first of all be explained in detail below:

A claw coupling is understood as a device which, in an open position, permits a rotation movement of the bearing bodies relative to each other and, in a coupling position, couples the bearing bodies in a rotationally fixed manner to each other. It is not necessary for the claw coupling to comprise a multiplicity of protrusions. It can also comprise just one protrusion, which can interact with a recess on the claw coupling. The design of the protrusions can be adapted to the desired initial, transitional and final mobility of the bearing bodies. The protrusions can be designed, for example, as claws, teeth or cylindrical or conical pins. The important thing is that the protrusions arranged on the upper and lower bearing bodies can be brought into form-fit engagement with one another.

An initial open position is understood as an expanded arrangement of the claw coupling which permits a movement of the bearing bodies relative to each other. The blocking body is not deformed in the open position, such that the protrusions of the claw coupling do not engage in one another and permit a free rotation of the bearing bodies relative to each other. The implant also has its maximum height in the open position.

A final coupling position is understood as a compressed arrangement of the upper and lower bearing bodies and also of the central piece, in which arrangement the bearing bodies are coupled to each other. The claw coupling is closed in the final coupling position. Despite the closed claw coupling, a residual mobility may optionally remain between the bearing bodies. The implant has its minimum height in the coupling position.

A slow plastic deformation is understood as an irreversible change of shape of a body, this change taking place in a time interval of longer than one hour, preferably at most 24 months. A slow deformation accordingly has a large time constant.

A free movement of the bearing bodies is understood as a movement which is limited only by the ligaments of the spinal column or by other anatomical circumstances, but not by the claw coupling.

The core of the invention is to transfer the claw coupling of the implant from an open position to a coupling position by means of a slow plastic deformation of the blocking body. By virtue of the initial open position of the implant, a patient is able to turn his spinal column without restriction in the days following the implantation. The blocking body is not deformed in the movement position, such that the protrusions of the claw coupling do not engage in one another. Therefore, the vertebrae connected by the implant can be rotated relative to each other. Because of the load acting on the implant in the spinal column of the patient, a pressure force is exerted on the blocking body. This force plastically deforms the blocking body, wherein the blocking body is designed such that the plastic deformation is effected slowly. The deformation of the blocking body causes a gradual transfer of the implant from the open position to the coupling position, and a compression of the implant. During the transfer, the open position and the coupling position overlap. In this overlap phase, the blocking body is not yet completely deformed and causes a partial closure of the claw coupling. The protrusions of the claw coupling do not completely engage in one another in this phase and can therefore be rotated relative to one another through a limited angle. Therefore, the bearing bodies and the vertebrae bearing on them can no longer freely rotate relative to each other in the overlap phase. Rotation is still possible only up to a maximum angle of rotation. Greater deformation of the blocking body reduces the maximum angle of rotation. This means that the mobility of the implant continuously decreases until, finally, the coupling position is reached.

In the coupling position, the protrusions of the claw coupling are arranged such that they engage in one another. Therefore, the claw coupling is closed in the coupling position, and the vertebrae connected by the implant are coupled. It will be noted that a small residual mobility may optionally remain in the coupling position. Moreover, it is not essential that bearing body and central piece are separate parts. They can also merge one into the other.

As a result of the slow transfer from the open position to the coupling position, the patient is therefore not confronted with a sudden limitation to the freedom of movement of his spinal column. The fusing of the vertebrae is therefore not obvious to the patient. Moreover, as a result of the slow limitation of the mobility in the overlap phase, the locomotor apparatus of the patient has sufficient time to adapt itself to the new situation. This reduces the load on the locomotor apparatus, the fused vertebrae and the implant.

The claw coupling advantageously has protrusions which are arranged on the upper and lower bearing pieces, and which face toward the respective other bearing piece.

Advantageously, the blocking body is integrated in the central piece, wherein the blocking body is preferably modular and exchangeable and/or is preferably designed as a disk. In this way, the time constant of the deformation can be easily adjusted by means of the thickness of the blocking body. The protrusions of the claw coupling can be arranged to slide on the blocking body. Moreover, the deformation of the blocking body has the effect that the path along which the protrusions can slide on the blocking body is limited. The protrusions engage in one another as a result of the deformation. As a result of the load of the spinal column, they impart an undulating shape to a blocking body that is designed as a disk. In this case, during a rotation of the bearing bodies, the protrusions therefore have to slide on an undulating disk, as a result of which the path along which they can travel on a plane surface is reduced in size.

Moreover, the protrusions are advantageously designed for self-centering and rotation braking in the coupling position, wherein the plastically deformed blocking body functions as a rotation brake. The protrusions are preferably rounded for this purpose. A rounded protrusion has the effect that the part of the deforming blocking body which limits the movement of the protrusion is transferred into a rounded shape and avoids damage. Moreover, by way of the rounded protrusion, the deformed blocking body acts as a steplessly increasing rotation brake. The rounded protrusions slide in the rounded part of the blocking body as in a trough, as a result of which they are centered. At the limits of the trough, the sliding movement of the protrusions causes an opening of the claw coupling. The implant therefore has to be expanded for a rotation that guides the protrusions past the limit. This is made difficult by the ligaments and by the load of the spinal column, which thus act as a soft abutment.

In a first preferred embodiment, the intervertebral fusion implant has an axial upper pin arranged on the blocking body, which axial upper pin is arranged in an axial bore of the upper bearing body, and an axial lower pin arranged on the blocking body, which axial lower pin is arranged in an axial bore of the lower bearing body. The pins act, in combination with the axial bores, as an inner guide for the blocking body. They center the blocking body between the bearing bodies and prevent the blocking body from being forced away from the bearing bodies.

In a second preferred embodiment, the intervertebral fusion implant has a collecting trough, which is preferably designed as a belt extending around the claw coupling. The collecting trough also functions as an outer guide, which centers the blocking body between the bearing bodies. The collecting trough also catches abrasion material which arises as a result of the initial mobility of the claw coupling, such that said abrasion material cannot migrate into the surrounding tissue. Complications after the implantation are thus avoided.

In a third preferred embodiment, the intervertebral fusion implant comprises upper and lower grooves which extend radially around the blocking body, wherein the protrusions are arranged in the groove. In this embodiment, the groove functions as a guide for the protrusions and as a centering aid for the blocking body.

Advantageously, the upper and lower bearing bodies are of identical design in a fourth preferred embodiment. This permits cost-effective production and simplifies the assembly of the implant.

In a fifth preferred embodiment, the upper bearing body advantageously has an upper holding module, and the lower bearing body has a lower holding module.

It is expedient if the claw coupling on each bearing body has four or more protrusions. This achieves a high degree of stability of the implant with respect to tilting movements of the spinal column.

The bearing bodies advantageously have bearing surfaces with a coating that promotes growth of bone. The coating causes a rapid incorporation of the vertebrae in the bearing bodies arranged on them. This increases the stability of the implant and of the final fusion.

Moreover, the intervertebral fusion implant in the coupling position advantageously has a height of between 3 mm and 9 mm, preferably 6 mm, and in the open position has a height of between 9.5 mm and 20 mm, preferably 12.5 mm, and it has a diameter of between 12 mm and 30 mm, wherein the blocking body has a thickness of between 0.5 mm and 3 mm. The thickness of the blocking body is understood as the spatial extent along the rotation axis of the claw coupling.

The blocking body is expediently made of a tough plastic that promotes sliding, in particular PEEK or UHMWPE.

Moreover, the bearing bodies and the protrusions are expediently made of a biocompatible metal alloy, in particular of pure titanium, a titanium alloy, a cobalt-based alloy CoCr or CoCrMo, or of a high-strength biocompatible plastic, in particular PEEK, PEEK-carbon or ceramic.

The invention further relates to a system composed of an intervertebral fusion implant for the fusion of two vertebrae, comprising an upper bearing body for placing on a lower end-plate of a vertebra, and a lower bearing body for placing on an upper end-plate of an opposite vertebra, and also a central piece arranged between the bearing bodies, and of forceps with a mouth having first and second jaw elements, wherein the central piece is designed as a claw coupling which, in a coupling position, couples the two bearing bodies in a rotationally fixed manner to each other, wherein, in an open position of the claw coupling, the bearing bodies are freely movable in relation to each other, wherein the claw coupling is actuated automatically and has, as actuating member, a plastic blocking body which, in its initial position, holds the claw coupling open and, under a load transferred from one vertebra to the other vertebra, is slowly deformable until it reaches a final coupling position, in which the claw coupling is closed; and the jaw elements are designed for the positionally offset arrangement of the protrusions on the upper and lower bearing bodies, such that the protrusions of the upper bearing body are arranged next to the protrusions of the lower bearing body.

As a result of the positionally offset arrangement, the protrusions are positioned in a tooth-on-gap arrangement when the spinal column is not subjected to rotation. This ensures that the implant fuses the vertebrae bearing on it in a non-rotated state.

The forceps advantageously have an abutment element for setting a minimum distance between the jaw elements, wherein the jaw elements receive the intervertebral fusion implant in the open position. This prevents the blocking body from being deformed by the force of the forceps even before implantation.

As regards developments of the intervertebral fusion implant, reference is made to the preceding description.

The invention further relates to a method for the fusion of two vertebral bodies by means of an intervertebral fusion implant for the fusion of two vertebrae, said implant comprising an upper bearing body for placing on a lower end-plate of a vertebra, and a lower bearing body for placing on an upper end-plate of an opposite vertebra, and also a central piece arranged between the bearing bodies, wherein the central piece is designed as a claw coupling which, in a coupling position, couples the two bearing bodies in a rotationally fixed manner to each other, wherein, in an open position of the claw coupling, the bearing bodies are freely movable in relation to each other, wherein the claw coupling is actuated automatically and has, as actuating member, a plastic blocking body which, in its initial position, holds the claw coupling open and, under a load transferred from one vertebra to the other vertebra, is slowly deformable until it reaches a final coupling position, in which the claw coupling is closed, said method comprising the following steps: preparing an implantation site, inserting the intervertebral fusion implant in the expanded open position into the implantation site, and closing the implantation site.

The insertion of the intervertebral fusion implant is expediently performed by means of forceps comprising a mouth with first and second jaw elements, wherein the jaw elements are designed for the positionally offset arrangement of the protrusions, such that the protrusions of the upper bearing body are arranged next to the protrusions of the lower bearing body.

The implantation site is advantageously designed to receive the intervertebral fusion implant in the expanded open position.

As regards developments of the intervertebral fusion implant and of the forceps, reference is made to the preceding description.

BRIEF DESCRIPTION OF THE DRAWINGS

The invention is explained in more detail below with reference to the attached drawing, which depicts an advantageous embodiment. In the drawing.

DETAILED DESCRIPTION OF THE INVENTION

Figure 1A:
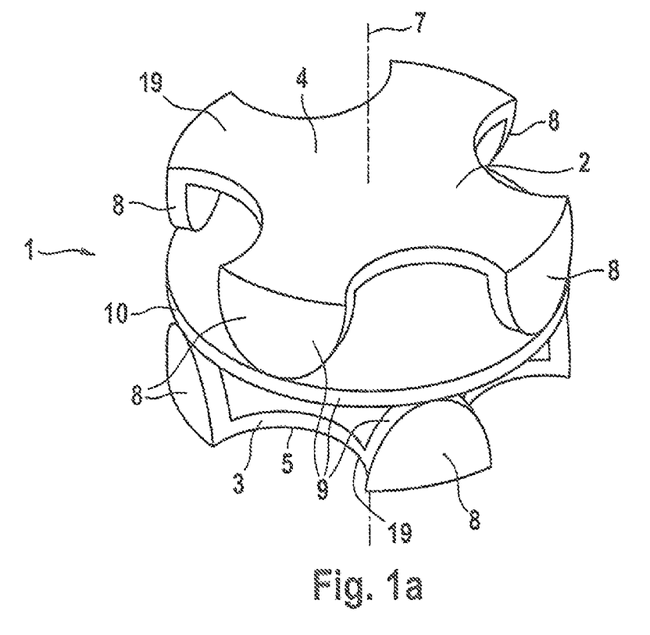
FIGS. 1a, b show schematic views of an intervertebral fusion implant, with an integrated blocking body in the non-deformed state (a) and in the deformed state (b)
Figure 1B:
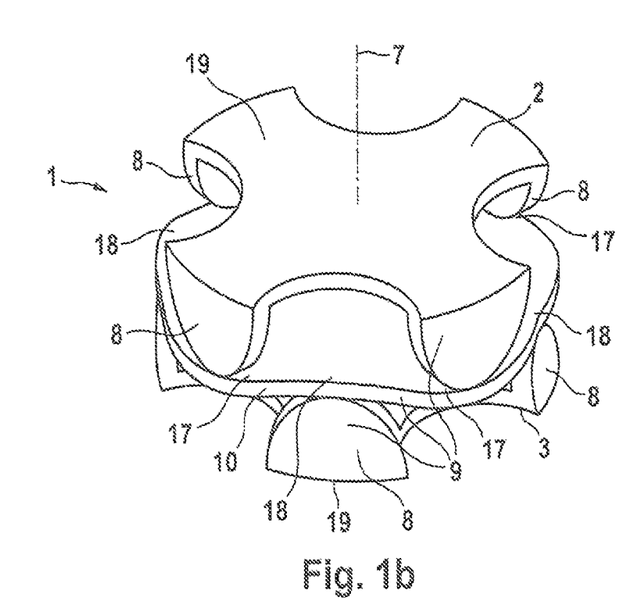

The intervertebral fusion implant is designated in its entirety by reference number 1. It has an upper bearing body 2, a lower bearing body 3, and a claw coupling 9 arranged between the bearing bodies 2, 3. The bearing bodies 2, 3 are designed to be arranged on the lower and upper cover plate, respectively, of a vertebra 52, 53. For this purpose, they have bearing surfaces 4, 5. A rotation axis 7 of the claw coupling 9 is arranged transversely with respect to the cover plates of the vertebrae 52, 53. Moreover, four protrusions 8 of the claw coupling 9 are arranged on each of the bearing bodies 2, 3 and face toward the respective other bearing body 2, 3. The protrusions 8 are rounded. They are also arranged to slide on a blocking body 10, such that they can perform a rotation about the rotation axis 7. By means of the claw coupling 9, the bearing bodies 2, 3 can thus be rotated relative to each other about the rotation axis 7 in the open position. A modular and exchangeable blocking body 10 is integrated in the claw coupling 9 and can slowly be plastically deformed.

Figure 4:
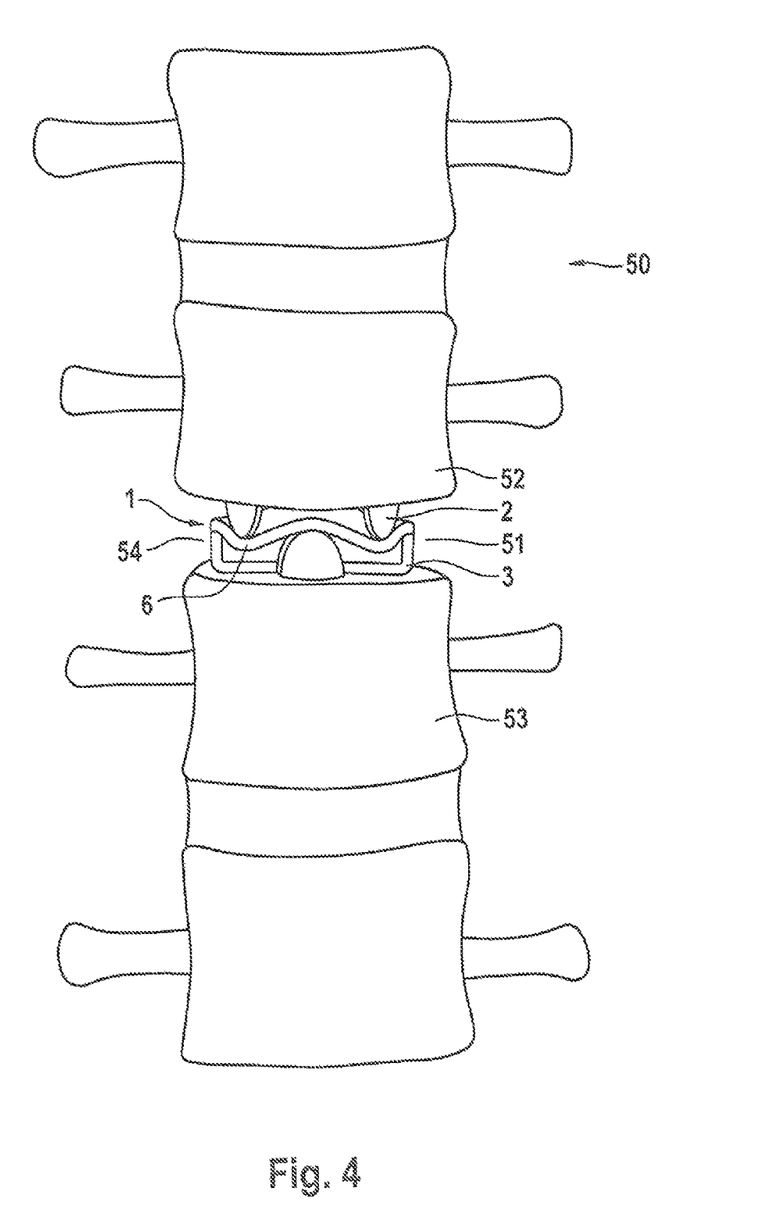
FIG. 4 shows a schematic view of part of a spinal column, with the intervertebral fusion implant inserted.

In the initial expanded and open position, the intervertebral fusion implant 1 is fitted in an intervertebral space 51 of a patient. In the movement position, the protrusions 8 of the upper bearing body 2 are arranged at an offset with respect to the protrusions 8 of the lower bearing body 3. The load carried by the spinal column 50 causes a pressure force to act on the intervertebral fusion implant 1 in the intervertebral space 51. The pressure force is transferred from the upper bearing body 2 to the protrusions 8 arranged thereon. By way of the contact between the protrusions 8 and the blocking body 10, the pressure forces act on the blocking body 10 from above. As a result of the offset positioning of the protrusions 8 of the upper and lower bearing bodies 2, 3, the blocking body 10 has pressure positions 17 where the protrusions 8 arranged on the upper bearing body 2 exert a force on the blocking body 10. Moreover, the blocking body 10 has support positions 18 where the protrusions 8 arranged on the lower bearing body 3 support the blocking body 10. At the pressure positions 17, the blocking body 10 is slowly plastically deformed, with the protrusions 8 forcing a depression into the blocking body 10 relative to the support positions 18.

As soon as the plastic deformation begins, the intervertebral fusion implant 1 is compressed. In order to move the protrusions 8 of the upper bearing body 2 transversely with respect to a depression in the direction of a support position 18, the intervertebral fusion implant 1 has to be expanded. For this movement, the intervertebral space 51 thus has to be enlarged through the patient. However, an enlargement of the intervertebral space 51 is made difficult by the ligaments (not shown) arranged on the spinal column 50 and by the load that bears on the spinal column 50. The intervertebral space 51 has to be more and more enlarged the closer a protrusion 8 arranged on the upper bearing body 2 approaches a support position 18. The resistance that the patient has to overcome when turning thus also increases, such that the blocking body 10 acts as a steplessly increasing rotation brake on the claw coupling 9. The same applies analogously to a movement of the protrusions 8 of the lower bearing body 3 in the direction of a pressure position 17.

As soon as the depressions are so pronounced that a movement of the protrusions 8 is no longer possible, the intervertebral fusion implant 1 is situated in the coupling position. The claw coupling 9 is completely closed in the coupling position. The protrusions 8 of the upper and lower bearing bodies 2, 3 engage in one another in the coupling position, such that a protrusion 8 of the upper bearing body 2 is arranged between two protrusions 8 of the lower bearing body 3, and vice versa. The vertebrae 52, 53 lying on the bearing bodies 2, 3 can move relative to each other about the rotation axis 7 only to the extent of a slight residual mobility. The vertebrae 52, 53 are thus fused.

To fix the intervertebral fusion implant 1 to the vertebrae 52, 53, the bearing bodies 2, 3 can have a substance that promotes the growth of bone. For this purpose, the substance is applied as a coating 19 on the bearing surfaces 4, 5. By means of the coating 19, the bearing bodies 2, 3 connect to the end-plates of the vertebrae 52, 53 and are fixed at their position. The danger of the intervertebral fusion implant 1 slipping is thus minimized.

Figure 2A:
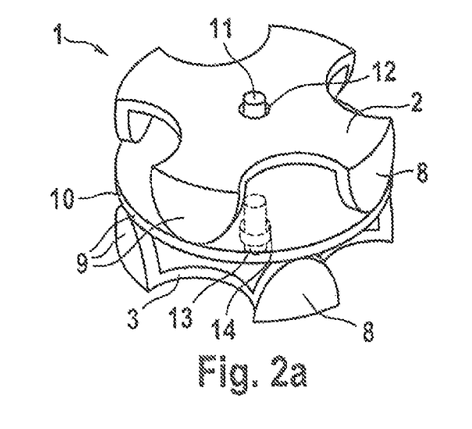
FIGS. 2a-c show schematic views of an intervertebral fusion implant with inner guide (a), outer guide (b), and groove (c)

A first embodiment of the intervertebral fusion implant 1 is shown in FIG. 2a. The bearing bodies 2, 3 have axial bores 12, 14 into which an upper pin 11 and lower pin 13 projecting from the blocking body 10 are arranged. The bores 12, 14 form a guide for the pins 11, 13, such that the blocking body 10 cannot perform any movement in the radial direction. The pins 11, 13, like the blocking body 10, are made of a plastically deformable material. By means of the pins 11, 13, the blocking body 10 is centered between the bearing bodies 2, 3, and the bearing bodies 2, 3 are mounted rotatably relative to the blocking body 10.

Figure 2B:
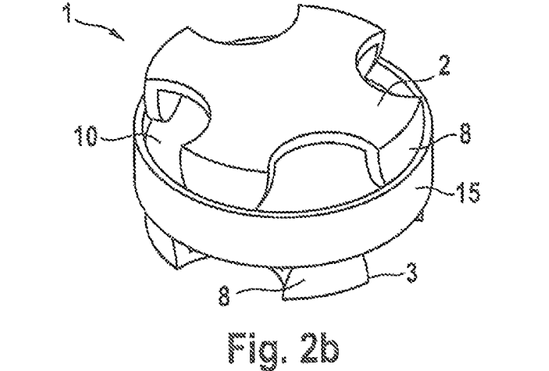

In a second embodiment, shown in FIG. 2b, the intervertebral fusion implant 1 has a collecting trough 15 which is arranged in the shape of a collar around the blocking body 10. The collecting trough 15 is designed as a belt. For the protrusions 8 arranged on the blocking body 10, the collecting trough 15 forms a limit in the radial direction. The collecting trough 15 thus prevents the blocking body 10 from being forced away from the bearing bodies 2, 3 in the radial direction. Moreover, the collecting trough 15 catches abrasion material that arises, during a movement of the intervertebral fusion implant 1, as a result of the friction between the protrusions 8 and the blocking body 10. In this way, the abrasion material cannot migrate into the surrounding tissue and cause complications there, e.g. inflammation.

Figure 2C:
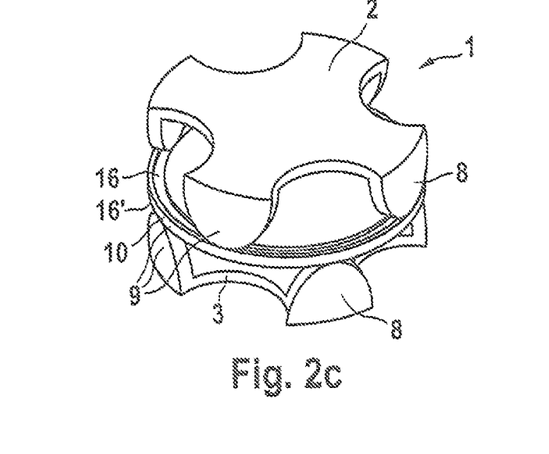

A third embodiment of the intervertebral fusion implant 1, shown in FIG. 2c, has grooves 16, 16' which are arranged on the blocking body 10, and in which the ends of the protrusions 8 are arranged. The grooves 16, 16' form a guide for the protrusions 8 and prevent slipping of the blocking body 10 from the bearing bodies 2, 3.

Figure 5A:
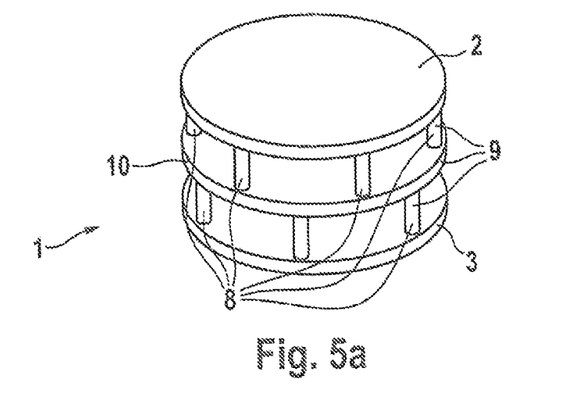
FIGS. 5a-c show schematic views of the intervertebral fusion implant in different embodiments.
Figure 5B:
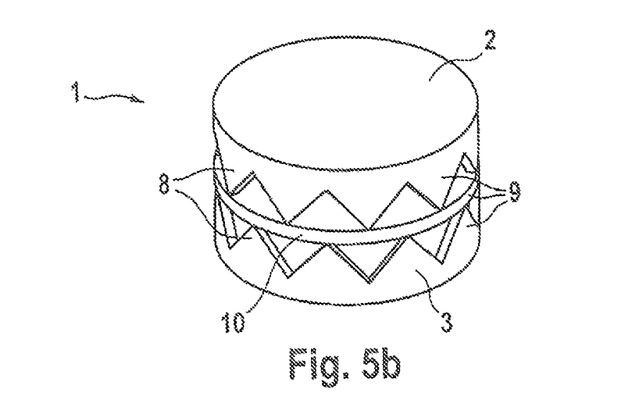
Figure 5C:
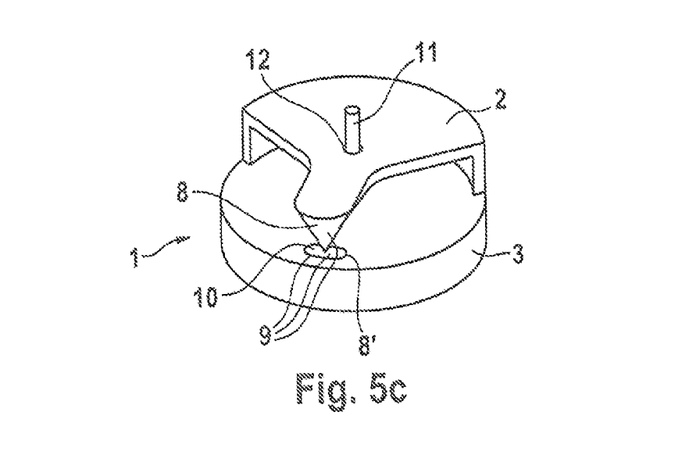

FIGS. 5a to 5c show further embodiments of the intervertebral implant 1 in which the protrusions 8 are not shaped like claws as described above. The protrusions 8 are designed as cylindrical pins in FIG. 5a and as gearwheel teeth in FIG. 5b. FIG. 5c shows an embodiment of the intervertebral implant 1 in which the claw coupling 9 has a single protrusion 8, designed as a conical pin, on the upper bearing body 2. Between the protrusion 8 and the lower bearing body 3, the blocking body 10 is arranged in a recess 8' of the lower bearing body 3. Through the loading force of the spinal column 50, the protrusion 8 slowly deforms the blocking body 10 plastically. As a result of the deformation of the blocking body 10, the protrusion 8 sinks into the recess 8', and the claw coupling 9 is gradually closed. The upper and lower bearing bodies are coupled in this way.

The blocking body 10 is made of UHMWPE. UHMWPE has a smooth surface and is slowly plastically deformable by the abovementioned measures. Moreover, the bearing bodies 2, 3 and the protrusions 8 are made of a titanium alloy. Titanium alloys are biocompatible and have a very good corrosion resistance within the body of a patient.

In the coupling position, the intervertebral fusion implant 1 has a height of between 3 mm and 9 mm, preferably 6 mm. In the open position, it has a height of between 9.5 mm and 20 mm, preferably 12.5 mm. The blocking body 10 in this case has a thickness of between 0.5 mm and 3 mm. The diameter of the intervertebral fusion implant 1 is between 12 mm and 30 mm. By means of the thickness of the blocking body 10 with the integrated blocking body 10, the time constant of the slow plastic deformation is fixed. The thicker the blocking body 10, the greater the time constant of the deformation.

Figure 3:
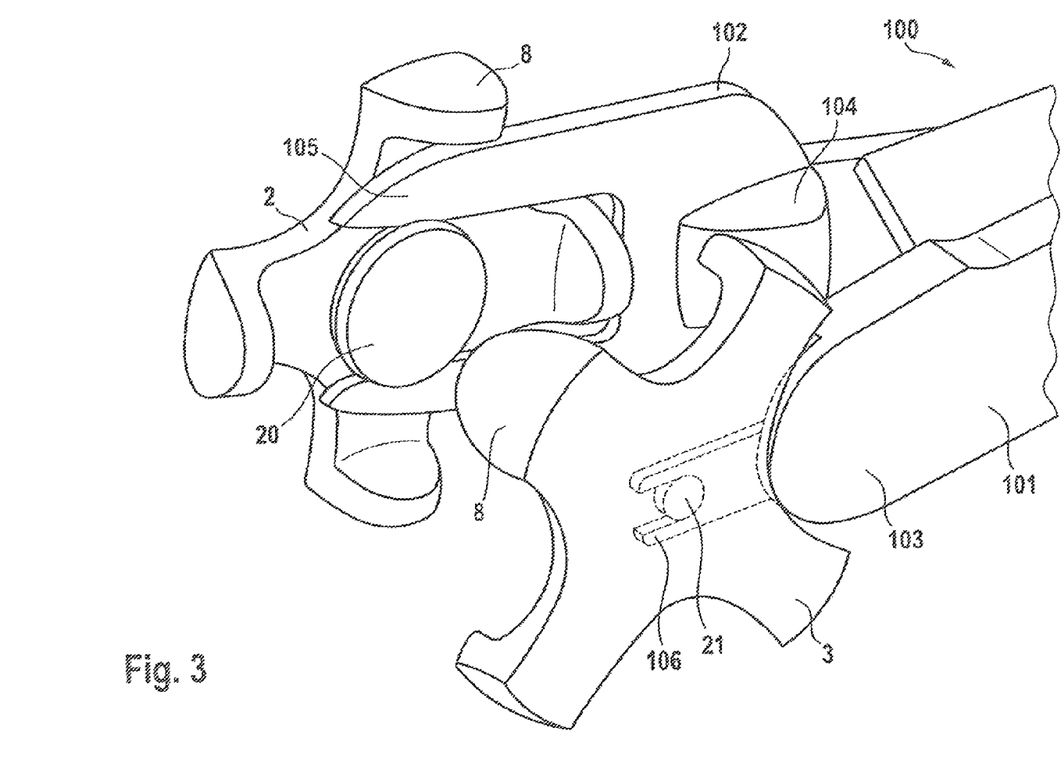
FIG. 3 shows a schematic view of forceps gripping the bearing bodies.

To be inserted into the intervertebral space 51 of a patient, the intervertebral fusion implant 1 can be gripped by forceps 100. For this purpose, the upper bearing body 2 can have an upper holding module 20, and the lower bearing body 3 can have a lower holding module 21. The forceps 100 have a mouth 101, which comprises a first jaw element 102 and second jaw element 103. The first jaw element 102 has a first grip module 105, which is designed to match a protrusion 8 in such a way that it can engage around a protrusion 8 from the radial direction. Moreover, the first grip module 105 is designed to grip the upper holding module 20. The second jaw element 103 has a second grip module 106. The second grip module 106 is designed to engage radially between two protrusions 8 of the lower bearing body 3 and to grip the lower holding module 21. The protrusions 8 of a bearing body 2, 3 that is gripped by the first jaw element 102, and the protrusions 8 of a bearing body 2, 3 that is gripped by the second jaw element 103, are therefore arranged in an offset position relative to one another about the rotation axis 7. The protrusions 8 of one bearing body 2, 3 then point between the protrusions 8 of the opposite bearing body 2, 3. When the intervertebral fusion implant 1 is held by means of the forceps 100, it is in the open position.

The forceps 100 further comprise an abutment element 104, which sets a minimum distance between the jaw elements 102, 103. The abutment element 104 can be arranged in the mouth 101 of the forceps 100. The abutment element 104 prevents the blocking body 10 from being deformed by the pressure of the forceps 100 on the intervertebral fusion implant 1.

The implantation of the intervertebral fusion implant 1 involves a first step in which an implantation site 54 is prepared on the patient. The surgeon exposes the intervertebral space 51 with the defective intervertebral disk and removes the intervertebral disk. The intervertebral space 51 is then optionally widened such that the intervertebral fusion implant 1 can be inserted into it in the expanded open position. The widening can be obtained by drawing the vertebrae 52, 53 apart or by extraction of bone substance. With the forceps 100, the intervertebral fusion implant 1 is inserted in the open position into the intervertebral space 51. The implantation site 54 is then closed.

The invention claimed is:
1. An intervertebral fusion implant for the fusion of two vertebrae comprising an upper bearing body for placing on a lower end-plate of a vertebra, a lower bearing body for placing on an upper end-plate of an opposite vertebra, and a central piece arranged between the bearing bodies, wherein the central piece comprises a claw coupling which, in a coupling position, couples the two bearing bodies in a rotationally fixed manner to each other, wherein, in an open position of the claw coupling, the bearing bodies are freely movable relative each other, and wherein the claw coupling is automatically actuatable and comprises an actuating member comprising a plastic blocking body which, in its initial position, holds the claw coupling open and, under a load transferred from one vertebra to the other vertebra, is slowly deformable until it reaches a final coupling position in which the claw coupling is closed.

2. The intervertebral fusion implant of claim 1, wherein the claw coupling comprises protrusions which are arranged on the upper and lower bearing bodies and which face toward the respective other bearing body.

3. The intervertebral fusion implant of claim 2, wherein the protrusions are configured for self-centering and rotation braking in the coupling position, and wherein the plastically deformed blocking body functions as a rotation brake.

4. The intervertebral fusion implant of claim 3, wherein the protrusions are rounded.

5. The intervertebral fusion implant of claim 2, wherein the intervertebral fusion implant comprises upper and lower grooves which extend radially around the central piece, wherein the protrusions are arranged in the grooves.

6. The intervertebral fusion implant of claim 1, wherein the blocking body is integrated in the central piece.

7. The intervertebral fusion implant of claim 6, wherein the blocking body is modular and exchangeable.

8. The intervertebral fusion implant of claim 6, wherein the blocking body comprises a disk.

9. The intervertebral fusion implant of claim 1, wherein the intervertebral fusion implant comprises an axial upper pin arranged on the blocking body, the axial upper pin being arranged in an axial bore of the upper bearing body, and an axial lower pin arranged on the central piece, the axial lower pin being arranged in an axial bore of the lower bearing body.

10. The intervertebral fusion implant of claim 1, wherein the intervertebral fusion implant comprises a collecting trough.

11. The intervertebral fusion implant of claim 10, wherein the collecting trough comprises a belt extending around the claw coupling.

12. The intervertebral fusion implant of claim 1, wherein the upper and lower bearing bodies are of identical design.

13. The intervertebral fusion implant of claim 1, wherein the upper bearing body comprises an upper holding module and the lower bearing body comprises a lower holding module.

14. The intervertebral fusion implant of claim 1, wherein each bearing body comprises four or more protrusions.

15. The intervertebral fusion implant of claim 1, wherein the bearing bodies comprise bearing surfaces with a coating that promotes growth of bone.

16. The intervertebral fusion implant of claim 1, wherein the intervertebral fusion implant in the coupling position has a height of between 3 mm and 9 mm, in the movement position has a height of between 9.5 mm and 20 mm, and has a diameter of between 12 mm and 30 mm, and wherein the blocking body has a thickness of between 0.5 mm and 3 mm.

17. The intervertebral fusion implant of claim 1, wherein the blocking body is made of a tough plastic that promotes sliding.

18. The intervertebral fusion implant of claim 17, wherein the blocking body is made of PEEK or UHMWPE.

19. The intervertebral fusion implant of claim 1, wherein the bearing bodies and the claw coupling are made of a biocompatible metal alloy, pure titanium, a titanium alloy, a cobalt-based alloy CoCr or CoCrMo, or of a high-strength biocompatible plastic, PEEK, PEEK-carbon or ceramic.

20. The intervertebral fusion implant of claim 1, wherein the intervertebral fusion implant in the coupling position has a height of 6 mm, in the movement position has a height of 12.5 mm, and has a diameter of between 12 mm and 30 mm, and wherein the blocking body has a thickness of between 0.5 mm and 3 mm.

21. A system comprising an intervertebral fusion implant for the fusion of two vertebrae, the intervertebral fusion implant comprising an upper bearing body for placing on a lower end-plate of a vertebra, a lower bearing body for placing on an upper end-plate of an opposite vertebra, and a central piece arranged between the bearing bodies, and forceps with a mouth having first and second jaw elements, wherein the central piece comprises a claw coupling which, in a coupling position, couples the two bearing bodies in a rotationally fixed manner to each other, wherein, in an open position of the claw coupling, the bearing bodies are freely movable relative to each other, wherein the claw coupling is automatically actuatable and comprises an actuating member comprising a plastic blocking body which, in its initial position, holds the claw coupling open and, under a load transferred from one vertebra to the other vertebra, is slowly deformable until it reaches a final coupling position in which the claw coupling is closed, and wherein the jaw elements are configured for a positionally offset arrangement of protrusions on the upper and lower bearing bodies such that the protrusions of the upper bearing body are arranged next to the protrusions of the lower bearing body.

22. The system of claim 21, wherein the forceps comprise an abutment element for setting a minimum distance between the jaw elements, wherein the jaw elements receive the intervertebral fusion implant in the open position.

23. The system of claim 21, wherein the protrusions are arranged on the upper and lower bearing bodies and face toward the respective other bearing body.

24. A method for the fusion of two vertebral bodies using an intervertebral fusion implant for the fusion of two vertebrae, said implant comprising an upper bearing body for placing on a lower end-plate of a vertebra, a lower bearing body for placing on an upper end-plate of an opposite vertebra, and a central piece arranged between the bearing bodies, wherein the central piece comprises a claw coupling which, in a coupling position, couples the two bearing bodies in a rotationally fixed manner to each other, wherein, in an open position of the claw coupling, the bearing bodies are freely movable relative to each other, and wherein the claw coupling is automatically actuatable and comprises an actuating member comprising a plastic blocking body which, in its initial position, holds the claw coupling open and, under a load transferred from one vertebra to the other vertebra, is slowly deformable until it reaches a final coupling position in which the claw coupling is closed, said method comprising:
    preparing an implantation site;
    inserting the intervertebral fusion implant in the expanded open position into the implantation site; and
    closing the implantation site.

25. The method of claim 24, wherein the insertion of the intervertebral fusion implant is performed using forceps comprising a mouth with first and second jaw elements, wherein the jaw elements are configured for a positionally offset arrangement of protrusions on the upper and lower bearing bodies such that the protrusions of the upper bearing body are arranged next to the protrusions of the lower bearing body.

26. The method of claim 25, wherein the protrusions are arranged on the upper and lower bearing bodies and face toward the respective other bearing body.

27. The method of claim 25, wherein the forceps comprise an abutment element for setting a minimum distance between the jaw elements, wherein the jaw elements receive the intervertebral fusion implant in the open position.

28. The method of claim 24, wherein the implantation site is prepared to receive the intervertebral fusion implant in the expanded open position.

\* \* \* \* \*